(12) United States Patent
Ollar

(10) Patent No.: US 6,277,562 B1
(45) Date of Patent: *Aug. 21, 2001

(54) METHOD FOR PARAFFINOPHILIC ISOLATION AND IDENTIFICATION FROM A BODY SPECIMEN

(76) Inventor: Robert-A. Ollar, 122 Cornelia La., Milford, PA (US) 18337-7139

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/770,308

(22) Filed: Dec. 20, 1996

Related U.S. Application Data

(63) Continuation of application No. 08/504,983, filed on Jul. 20, 1995, now abandoned, which is a continuation-in-part of application No. PCT/US94/00831, filed on Jan. 21, 1994, which is a continuation-in-part of application No. 08/035,358, filed on Mar. 22, 1993, now abandoned, which is a continuation-in-part of application No. 08/011,479, filed on Jan. 26, 1993, now abandoned.

(51) Int. Cl.[7] .................................................. C12Q 1/68
(52) U.S. Cl. ..................... 435/6; 536/24.32; 435/253.1
(58) Field of Search .................. 435/6, 253.1; 536/24.32

(56) References Cited

U.S. PATENT DOCUMENTS 4,579,941 * 4/1986 Furutani et al. ...................... 536/27
4,649,111 * 3/1987 Keller et al. .......................... 435/89

OTHER PUBLICATIONS

Ollar et al., Tubercle, 71(1):23–28, Mar. 1990.*
Hurley, J. Clin. Microbiol. 27(7):1582–1587, Jul. 1989.*

* cited by examiner

Primary Examiner—Scott W. Houtteman

(57) ABSTRACT

A method of determining the presence of a paraffinophilic organism in a body specimen involves introducing portions of the body specimen into a plurality of receptacles (50–57) which contain a sterile broth and antibiotics. Subsequently, one paraffin coated slide (18) is introduced into each receptacle. After observing organism growth on the paraffin coated slides, at least one slide is subjected to an alcohol-acid fastness test to determine whether the organism is an alcohol-acid fast, an acid-fast organism or a non-acid-fast/non-alcohol-acid fast organism. If it is determined that an alcohol-acid fast organism is present on the first slide, a tellurite reduction assay is performed on a second slide to determine the possibility of a presence of paraffinophilic organism on the second slide. If the tellurite reduction assay results is a determination that there is a possibility of presence of a paraffinophilic organism on the second slide, at least one speciation assay on the third paraffin coated slide is performed to confirm the presence of a paraffinophilic organism on the third paraffin coated slide. Subsequently, DNA extraction is employed on at least one additional slide to determine whether a paraffinophilic organism is present in the body specimen.

12 Claims, 2 Drawing Sheets

METHOD FOR PARAFFINOPHILIC ISOLATION AND IDENTIFICATION FROM A BODY SPECIMEN

CROSS REFERENCE TO RELATED APPLICATIONS

This is a continuation of application Ser. No. 08/504,983, filed Jul. 20, 1995 now abandoned. This application is a continuation-in-part of Patent Cooperation Treaty application Ser. No. PCT/US94/00831, filed Jan. 21, 1994, which was a continuation-in-part of U.S. patent application Ser. No. 08/035,358, filed Mar. 22, 1993, abandoned, and entitled "A METHOD FOR PARAFFINOPHILIC ISOLATION AND IDENTIFICATION FROM A BODY SPECIMEN", which was a continuation-in-part of U.S. patent application Ser. No. 08/011,479, filed on Jan. 26, 1993, abandoned, and entitled "A METHOD FOR MYCOBACTERIUM AVIUM INTRACELLULAR ISOLATION AND IDENTIFICATION FROM A FECAL SPECIMEN."

BACKGROUND OF THE INVENTION

1. Field Of The Invention

This invention relates to a method for speciating and identifying paraffinophilic materials.

2. Description Of The Prior Art

Human immunodeficiency virus type 1 or HIV causes acquired immunodeficiency syndrome ("AIDS") which is a fatal disease approaching epidemic proportions throughout the world. By current estimates, 110 million people will be infected with HIV by the year 2010. When AIDS develops, it is usually characterized by opportunistic infection, such as Pneumocystic pneumonia, Kaposi's sarcoma, lymphoma and *Mycobacterium avium intracellulare* complex (MAI).

It has been found that more than 80% of AIDS patients have MAI present in their bodies (J. M. Wallace et al., Mycobacterium avium complex in patients with AIDS—A Clinicopathologic Study. Chest 93 (5) 926–932 (1988)). Organisms of MAI prior to the AIDS epidemic were recognized as a rare form of pneumonia in patients with chronic lung infections (E. Wolinsky, Nontuberculous mycobacteria and associated diseases. Am. Rev. Respir. Dis. 1979, 119:107–59). Organisms of MAI comprise two closely related species, *M. avium* and *M. intracellulare,* which have minor virulence in the non-HIV host. By 1980, only 24 cases of MAI had been reported in the medical literature (C. R. Horsburgh, Jr. et al., Disseminated infection with Mycobacterium avium intracellulare. Medicine (Baltimore) 1985, 64:36–48). However, the epidemic of disseminated MAI infection is concurrent with the AIDS epidemic.

Studies have shown that disseminated MAI infection makes a substantial contribution to both morbidity and mortality in AIDS patients (C. R. Horsburgh, Jr. et al., The Epidemiology of Disseminated Nontuberculous Mycobacterial Infection in the Acquired immunodeficiency syndrome (AIDS). Am. Rev. Respir. Dis. 1989, 139:4–7).

Up to the present time, the most common source of isolating MAI clinically has been by means of the blood. Isolation techniques for determining the presence or absence of MAI in the patients'blood are known. One method involves using the BACTEC Radiometric System, which is a product of the Johnson Division of Becton and Dickenson. The system itself utilizes hemoculture tubes that contain Middlebrook 7H12 liquid broth plus 0.05% (v/v) sodium polyanethyl sulphonate in hemoculture vials. In addition, the 7H12 broth contains Carbon-14 labelled palmitic acid. In use, vials containing mycobacterial growth give off Carbon-14 labelled $CO_2$ and this is detected by a device similar to that used for liquid scintillation capable of detecting beta emitters. Another method of isolation in blood involves using genetic probes which rely upon DNA hybridization (C. M. Reichert et al., Pathologic features of AIDS. In: V. T. DeVita Jr. et al. (eds) AIDS etiology, diagnosis, treatment and prevention, p. 134 NY J. 13, Lipponcott, 1985).

However, when MAI becomes widely disseminated in AIDS patients the involvement by way of the blood of bone, lungs, spleen and the CNS causes an almost 100% rate of mortality (C. C. Hawkins et al., MAI in patients with acquired immunodeficiency syndrome. Am. Intern. Med. 1986; 105: 184–8) (J. Hoy et al., Quadruple drug therapy for Mycobacterium avium intracellulare bacteremia in AIDS patients. J. Infect. Dis. 990; 161: 801–5).

These known methods, although effective, require expensive equipment and specialized operating personnel and materials. Thus, smaller hospital centers where few AIDS patients are seen, field laboratories, and third world countries, where resources are limited, do not have this specialized equipment and personnel. A simpler and more inexpensive method and apparatus of isolating and identifying MAI would be of substantial benefit in such situations.

It is known that many atypical Mycobacteria grow on basal salt media devoid of any carbon sources other than paraffin wax which is introduced into the media in the form of paraffin was coated roads. Fuhs, G. W., "Der Mikrobiell Abbau Von Kohlenwasserstoffen", Arch. Mikrobiol. 39:374–422 (1961). Mishra, S. K. et al., "Observations On Paraffin Baiting As a Laboratory Diagnostic Procedure in Nocardiosis", Mycopathologica and Mycologia Applicata 51 (2–3): 147–157 (1973) utilized paraffin coated rods and basal salt medium to isolate Nocardia asteroides from clinical specimens such as sputum, bronchial lavage and cerebrospinal fluid.

The technique was further improved by substituting paraffin wax coated slides for rods and thereby making possible the use on an in situ Kinyoun cold acid-fastness staining procedure for organisms growing on the paraffin coated slide. Ollar, R. A., "A Paraffin Baiting Technique that Enables a Direct Microscopic View of in situ Morphology of Nocardia asteroides with the Acid-Fast or Fluorescence Staining Procedures", Zbl. Bakt. Hyg., Abt. Orig. A, 234: 81–90 (1976). With this assay, a positive reaction tells the user immediately that a mycobacteria organism other than *M. tuberculosis* is present.

U.S. Pat. No. 5,153,119, which names one of the joint inventors of the present invention as sole inventor, discloses a method for speciating and identifying MAI in a specimen and involves the use of paraffin coated slides to determine the presence or absence of atypical Mycobacteria (mycobacteria other than *M. tuberculosis, M. laprae,* and *M. paratuberculosis*). This process, while quite effective for isolating and speciating of MAI, may for some purposes be deemed to be relatively slow, taking on the order of about 6 days (in feces) to 34.5 days (in blood). The disclosure of this patent is expressly incorporated herein by reference.

As will be apparent from the foregoing, it is vital to human health that MAI be identified and treated as early as possible (C. A. Kemper et al., California Collaborative Group; Microbiologic and clinical response of patients with AIDS and MAC bacteremia to a four oral drug regimen; In: Program and abstracts of the 30th Interscience Conference on Antimicrobial Agents and Chemotherapy; Atlanta, Oct. 21–24, 1990; Washington D.C.; Am. Society for Microbiology; 1990; 297. abstract).

There is a real and substantial need for improved means of rapidly determining the presence of MAI and other paraffinophilic organisms in a patient.

SUMMARY OF THE INVENTION

As used herein, the term "paraffinophilic," means an organism that can employ paraffin wax as a source of carbon in a basal salt media, devoid of other forms of carbon. The organism may be bacterial or fungal in nature.

The present invention has met the above described need. It provides a method of determining the presence of a paraffinophilic organism in a body specimen by introducing portions of the specimen into a plurality of receptacles which contain a sterile broth and antibiotics. One paraffin coated slide is introduced into each receptacle with the slides being observed for the presence of organisms growing thereon. After observing such growth, a first slide is subjected to an alcohol-acid fastness test. If the result of this test determines that an alcohol-acid fast organism is present, a second slide is subjected to a tellurite reduction assay to determine the possibility of the presence of a paraffinophilic organism on the second slide. If it is determined that there is a possibility of the presence of a paraffinophilic organism on the second slide, a third slide is subjected to at least one speciation assay to confirm the presence of a paraffinophilic organism on the slide. Subsequently, a DNA extraction is employed on at least one additional slide to determine whether a paraffinophilic organism is present on the specimen. The DNA extraction procedure may be advantageously employed by anionic exchange column chromatography or organic solvent extraction.

It is an object of the present invention to isolate, identify and speciate paraffinophilic organisms in a body specimen in a rapid and reliable manner.

It is a further object of the invention to provide such a system which employs DNA extraction as a means for expediting prompt results.

It is a further object of the invention to provide a paraffinophilic organism specific simplified and rapid system which effects isolation and speciation of a paraffinophilic organism from fecal matter or other body specimens.

It is a further object of the present invention to employ the system of this invention in ascertaining whether a particular human has a paraffinophilic organism present.

It is a further object of the invention to provide a non-invasive method of detecting the presence of a paraffinophilic organism in a patient.

These and other objects of the invention can be more fully understood with reference to description and the drawings appended to this application.

DESCRIPTION OF THE PREFERRED EMBODIMENTS

Figure 1:
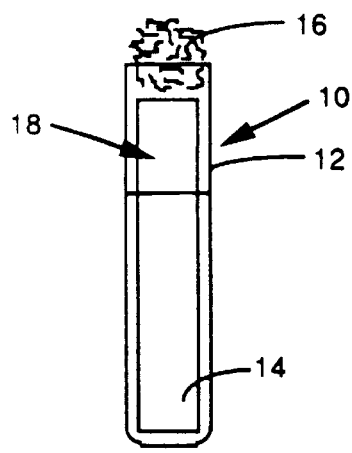
FIG. 1 is a schematic front elevational view of a receptacle holding a paraffin coated slide in a sterile aqueous solution containing the fecal specimen.

As used herein, the term "patient" refers to a member of the animal kingdom, including human beings, whose body specimen is being processed by the system of the present invention.

As used herein, the term "body specimen" shall include fecal matter, blood, sputum, tissue, and cerebral spinal fluid obtained from a patient.

As used herein, the term "paraffinophilic" shall expressly include, but not be limited to the following organisms: *Micrococcus paraffinae; Corynebacterium simplex;* Ahnl; *Mycococcus* (Rhodococcus) *cinnabareus;* Ahnl. *Mycococcus* (Rhodoc) *rhodochrous; Mycobact. perrugosum* Var. *athanicum; Mycobact. rubrum* Var. *propanicum; Mycobacterium hyalinum; Mycobacterium lacticola; Mycobacterium album, M. luteum; Mycobacterium microti; Mycobacterium rubrum, Mycobacterium phlei,; Mycobacterium phlei, M. smegmatis; Mycobacterium testudo; Mycobacterium-avium-intracellulare;* Nocardia Spp.; Actinomyces; *Candida lipolytica; Candida tropicalis, Torulopsis colliculosa;* Monilia Sp., Hansenula Sp., *torula rossa;* Penicillium Sp., IHNL. *Aspergillus flavus;* Aspergillus sp., Penicillium Sp.; Citromyces Sp., Scopulariopsis Sp., *Pseudomonas fluorescens liquefaciens;* Ahnl, Pem. *Fluorescens denitrificans; Pseudomonas aeruginosa.*

In addition to the MAI detection in fecal matter, it is important to be able to detect other paraffinophilic organisms in other body specimens in order to facilitate rapid and accurate diagnostic determination of conditions having significant impact on a patient's health. Paraffinophilic organism related opportunistic pathology may be detected by the present invention. For example, it is known that Hodgkin's disease has an adverse effect on cellular immunity, as does intentional immunosuppression employed in cellular, tissue, or organ transplants. Such conditions can lead to undesired opportunistic infections, the early detection of which can be of great importance to proper treatment of a patient. Among the most important categories of such paraffinophilic organisms are the mycobacterium, candida and nocardia species.

As indicated hereinbefore, it is vital to human health that MAI be identified and treated as early as possible (C. A. Kemper et al., California Collaborative Group; Microbiologic and clinical response of patients with AIDS and MAC bacteremia to a four oral drug regimen; In: Program and abstracts of the 30th Interscience Conference on Antimicrobial Agents and Chemotherapy; Atlanta, Oct. 21–24, 1990; Washington D.C.; Am. Society for Microbiology; 1990; 297. abstract).

The identification of MAI in fecal matter is advantageous in accomplishing this objective as MAI is initially found in the gastrointestinal tract (E. C. Klatt et al., Pathology of Mycobacterium avium-intracellulare infection in acquired immunodeficiency syndrome; Hum. Pathol. 1987; 18: 709–14). Colonization of the gastrointestinal tract precedes the ability to isolate MAI in the blood by many months and thereby offers an advantageous means for getting an early warning. Gut histopathology of AIDS patients reveals a large number of acid-fast bacilli in both the mucosal and submucosal layers of the gastrointestinal tract.

It will be appreciated that early detection of MAI can result in significant prolongation of the life of an AIDS patient.

The localized gastrointestinal infection occurs most commonly in the duodenum causing a lymphadenopathy. Additional areas of MAI infection are the terminal ileum and appendix. The increased number of Payer's patches increases local MAI concentrations. Ethanol ingestion is associated with a significant increase in MAI infection of the gastrointestinal tract. This is believed to be due to the enhanced passage of MAI across the intestinal wall secondary to an alcohol induced enteritis (L. E. Bermudez et al., An animal model of Mycobacterium avium complex disseminated infection after colonization of the intestinal tract; Kuzell Institute for Arthritis and Infectious Diseases; Medical Research Institute of San Francisco at California Pacific Medical Center 94115; J. Infect. Dis. January 1992; 165(1): 75–9). Symptoms involved in gastrointestinal traction infection are nausea, diarrhea, abdominal pain, biliary obstruction and severe cachexia.

The colonization of MAI of the gastrointestinal tract may be due to transmission through the water supply. Studies from Jefferson Medical College have documented colonization of that hospital's hot water system beginning in 1982. It was also found that colonization of normal volunteers could be demonstrated after they gargled with water from the hospital (S. A. Murphy et al., *Mycobacterium avium intracellulare* in a hospital hot water system: epidemiological investigation; In: Proceedings and abstracts of the 24th Interscience Conference on Antimicrobial Agents and Chemotherapy, Las Vegas, Oct. 24–26, 1983, Washington, D.C.; American Society for Microbiology, 1983; 277). The home water supply of HIV patients may be the potentially infectious source of initial transmission of MAI.

The HIV wasting syndrome is a clinically defined entity in which findings of profound involuntary weight loss greater than 10% of baseline body weight plus either chronic diarrhea (at least two loose stools per day for greater than or equal to 30 days) or chronic weakness and documented fever (for greater than or equal to 30 days, intermittent or constant) in the absence of concurrent illness or condition other than HIV infection that could explain the findings such as cancer, cryptosporidiosis, or other specific enteritis, for example, (P. Ma et al., AIDS and Infections of Homosexual Men Second Edition, Appendix 14-B; Stoneham, Mass.; Butterworths, 1989; 233–234) may be in large part a manifestation of MAI infection. The shortened survival time (median longevity: 4.1 months with disseminated MAI infection) (J. A. Havlik, Jr. et al., Disseminated Mycobacterium avium complex infection: clinical identification and epidemiologic trends; J. Infect. Dis. 1992; 165: 577–80) is presumed due to the severe loss of weight. In many cases, death has been found to result from inanition. It would, therefore, be advantageous to have monthly checks for MAI in all patients who meet the following reasonable criteria: 1) HIV positivity, 2) loss of weight greater than 5 lbs. or greater than 5% of body weight, and 3) a CD4 cell count under 400. If MAI is detected in the HIV patient's stool using the above criteria, the use of early aggressive antibiotic therapy has been shown to prevent dissemination. Recent therapy has involved the use of Ciprofloxacin with Ethambutol, Ansamycin and Clofazimine (C. B. Inderlied et al., Disseminated mycobacterium avium complex infection; AIDS Clin. Rev. 1990; 165–91). However, each individual HIV patient's antibiotic regimen would be guided by the use of antibiotic sensitivity testing such as that done by the MAI Para SL/C (Paraffin Slide Culture) method.

In the past, detection of these silent MAI infections of the G.I. tract in the ARC patient was very time consuming when the Lowenstein-Jensen, Middlebrook 7H9 and related Middlebrook media were used. Very lengthy protocols involving centrifugation, isolation and slow growth made these prior methods very impractical for use in the periodic testing of the G.I. tract in HIV patients for MAI. A simplified and inexpensive method specifically for handling contaminated fecal sample is needed for such periodic screening of HIV patients for MAI. The present invention includes an adaptation of the MAI Para SL/C method which we have designated as the MAI ParaPecogen method. The latter has been specifically designed for periodic testing of ARC patients and provides quick and inexpensive means of early detection of the presence of gastrointestinal in accordance with the above criteria.

The initial portion of the method of the present invention is the specific embodiment of that disclosed in Ollar, U.S. Pat. No. 5,153,119. In isolating the paraffinophilic organism from the body specimens, a suspension may be prepared by suspending a 4mm loopful of fresh body specimen in 3 to 5 milliliters of sterile saline. Employing a kit 10, a 0.5 milliliter specimen may be, as shown in FIG. 1, introduced into a test tube 12 which contains a sterile aqueous solution 14 (such as a Czapek broth) and a cotton plug 16 to seal the test tube. The specimen to be tested for the presence or absence of paraffinophilic organisms may be introduced into the test tube 12 and a paraffin coated slide 18 is subsequently analyzed. The paraffin coated slides may be made in accordance with the teachings of Ollar, U.S. Pat. No. 5,153,119. The Czapek broth 14 may be provided with an anti-bacterial, an anti-fungal/antibiotic cocktail such as that sold under the trade name "PANTA" sold by Becton, Dickenson/Johnston Labs Division. This product tends to resist possible contaminating factors such as *Pseudomonas aeruginosa* or *Candida tropicalis*. This product will have no effect on the paraffinophilic organism MAI which is resistant to the currently used antibiotic in "PANTA."

The kit 10 can also serve as a means of distinguishing between atypical mycobacteria and nocardioform organisms on the one hand and *mycobacteria tuberculosis* on the other hand because the latter cannot utilize paraffin was as a sole source of carbon. As is known, a tropism is created between the paraffin and organisms capable of using the paraffin as its carbon source, such as atypical paraffinophilic mycobacteria and paraffinophilic nocardioform organisms. The outward manifestation of this tropism or baiting is the appearance of growth on the paraffin surface.

Figure 2:
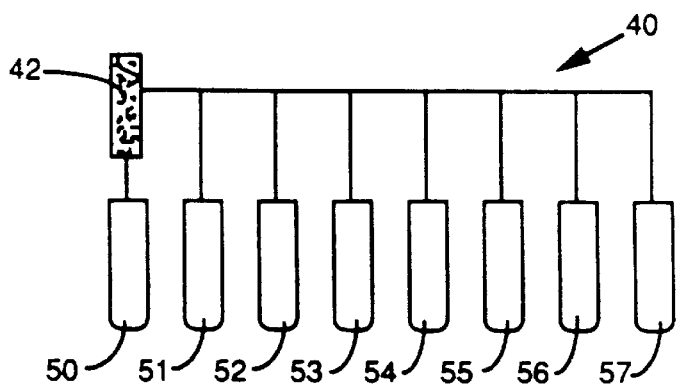
FIG. 2 is a schematic illustration of the acid-alcohol fastness assay employable in the present invention.

Paraffinophilic mycobacterial or nocardial presence on the slide is determined by an alcohol-acid fastness test 40 (FIG. 2). This test can be used to further distinguish between the atypical mycobacteria and the nocardioform organisms. As is known, atypical paraffinophilic mycobacteria are alcohol-acid fast; paraffinophilic nocardioform organisms are acid-fast and paraffinophilic *Pseudomonas aeruginosa* or paraffinophilic *Candida tropicalis* are neither acid nor alcohol-acid fast. Thus, these latter two paraffinophilic groups (nocardioforms and *Pseudomonas aeruginosa* or *Candida tropicalis*) can be eliminated as possibilities by the alcohol-acid fastness testing.

In isolating the paraffinophilic organisms as shown in FIG. 2, the eight test tubes 50, 51, 52, 53, 54, 55, 56, 57, are each provided with about 4.5 milliliters of sterile Czapek broth containing the antibacterial and anti-fungal/antibiotic cocktail as well as 0.5 ml of the fresh fecal suspension. A paraffin coated slide is then introduced into each of the body specimen inoculated Czapek broth antibiotic tubes 50–57 in a manner to be described hereinafter. The alcohol-acid fastness testing means 40 of FIG. 2 results in the solution staining the paraffinophilic organisms on the slide for subsequent analysis under a microscope. The receptacles or tubes 50–57 are incubated at about 37° C. When growth is observed, typically after about 24 to 96 hours, one of the slides is removed a tube and stained with Kinyoun Acid-alcohol stain as disclosed in U.S. Pat. No. 5,153,119. Another slide is withdrawn and subcultured in Lowenstein-Jensen media as disclosed in U.S. Pat. No. 5,153,119. A third slide is removed and tested for tellurite reduction as disclosed in U.S. Pat. No. 5,153,119. A further slide is removed and testing for nitrate reduction in accordance with U.S. Pat. No. 5,153,119. A further slide is removed and tested for urea hydrolysis in accordance with U.S. Pat. No. 5,153,119. Another slide is removed and tested for Tween 80 hydrolysis as disclosed in U.S. Pat. No. 5,153,119.

The paraffin coated slide culture with visible paraffinophilic organism growth 42 is removed from the test tube 12 of FIG. 1 and is first immersed in two consecutive tubes 50, 51 of distilled water and then immersed in a tube 52 of Kinyoun carbolfuchsin for fifteen minutes. The slide 42 is again immersed in a tube 53 of distilled water and then placed in a tube 54 containing acid-alcohol consisting of 97 ml absolute ethanol and 3.0 ml concentrated HCl for five minutes. After this, the slide is washed in a fourth tube 55 of distilled water and then placed into a tube 56 of 1.0% (v/v) aqueous Methylene blue solution for 1 minute. Finally, the slide is washed in a fifth tube 57 of distilled water.

The slide culture is then removed from the fifth tube 57 of distilled water and blotted gently with a clean absorbent paper tissue. the slide culture is then viewed under a microscope at 250×, 450× and 1000× oil immersion.

Figure 3:
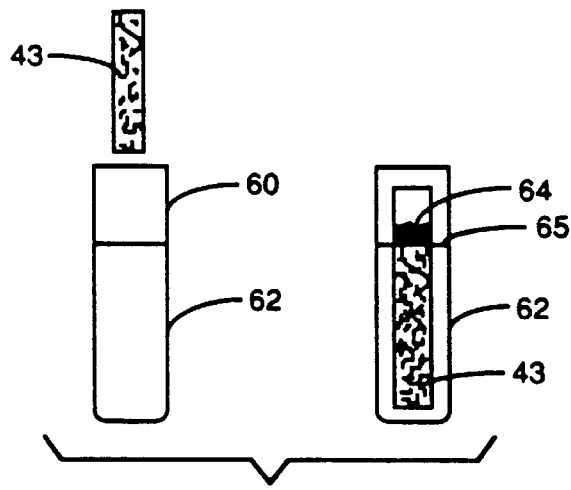
FIG. 3 is a schematic illustration of a tellurite reduction assay.

FIG. 3 shows the tellurite reduction assay which consists of a test tube 60 filled, preferably, with a Czapek broth plus an amount of potassium tellurite reagent 62. A cultured slide 43 is immersed into the test tube 60 and incubated. If a paraffinophilic MAI organism is present on the slide, a heavy black precipitate 64 forms at the level of the meniscus pellicle 65 of the slide 43. This test alerts the user to the possibility of paraffinophilic organism presence. Paraffinophilic MAI organism presence can be confirmed after the assay results are known for the assays discussed hereinafter.

Figure 4:
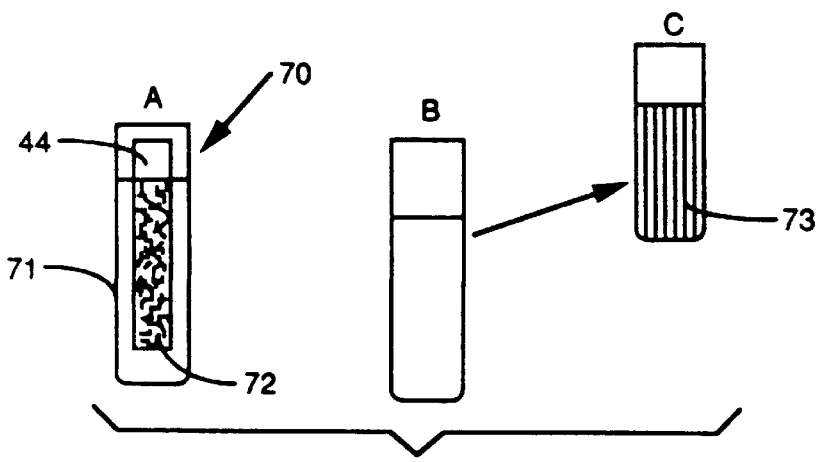
FIG. 4 is a schematic illustration of a nitrate reduction assay.

FIG. 4 shows the nitrate reduction assay 70. A slide culture 44 showing heavy growth is assayed for the ability to reduce nitrates to nitrites. This is done by adding nitrates to a tube 71 containing a sterile broth. After a period of 12 to 24 hours incubation at 37° C., the slide 44 is removed from the sterile nitrate broth 72 and five drops of sulfanilic acid reagent solution followed by five drops of alpha naphthylamine reagent solution are added to the tubes 71. The reduction of nitrate to nitrite appears as a red colored broth 73. As is known, if the nitrate is reduced to nitrite, this indicates the absence of paraffinophilic MAI organism on the slide.

Figure 5:
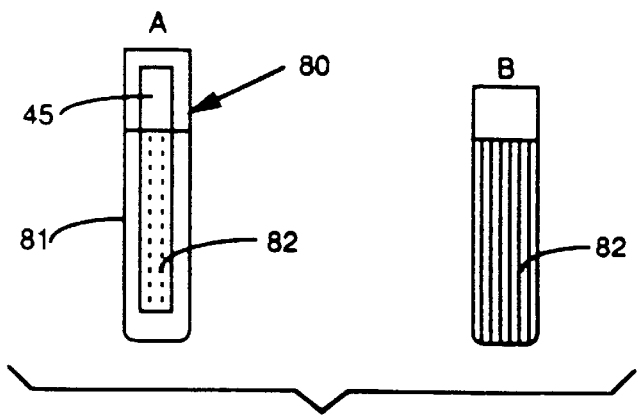
FIG. 5 is a schematic illustration of a urea hydrolysis assay.

FIG. 5 shows the urea hydrolysis reaction assay 80. A slide culture 45 is added to a plugged tube 81 containing 4.5 ml of sterile urea broth 82. The culture is incubated at 37° C. and checked after a period of three days. A positive reaction involves a color change of the broth 82 to pink or red after a period of three days. As is known, if the solution changes color, this indicates the absence of a paraffinophilic MAI organism on the slide 45.

Figure 6:
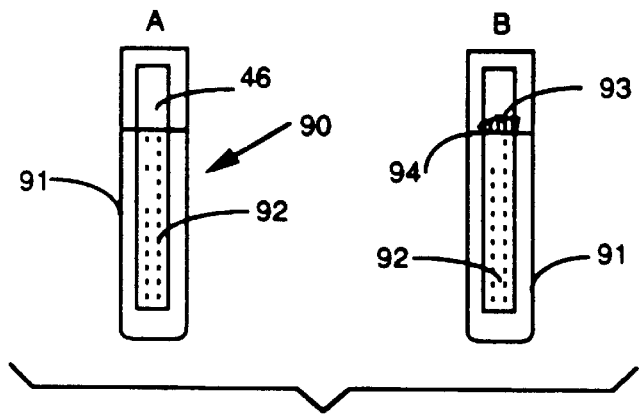
FIG. 6 is a schematic illustration of a Tween 80 hydrolysis.

FIG. 6 shows the emulsifier hydrolysis assay 90. The emulsifier used is "Tween 80," a trademark of Atlas Chemical Industries, Inc. and is generically described as polyoxyethylene derivatives of fatty acid partial esters of sorbitol anhydrides. A slide culture 46 was added to sterile plugged tubes 91 containing media 92 and incubated at 37° C. A positive reaction involved the appearance of a red coloration 93 on the meniscus pellicle 94 of the slide 46 within five days. As is known, the presence of the red coloration in the slide indicates the absence of a paraffinophilic organism on the slide.

It will be appreciated that at least the first three of the paraffinophilic MAI organism identification tests ((1) tellurite reduction, (2) nitrate reduction assay, (3) urea hydrolysis assay, or (4) "Tween 80," or hydrolysis emulsifier assay) should be performed, with the tellurite reduction test being the most important of the four tests. Preferably, all four of the tests should be performed in order to more accurately speciate and identify the paraffinophilic organism.

With the completion of these sequences, the basic speciation and isolation of paraffinophilic organism for a body specimen sample is completed. The final processing preferably involves DNA extraction. This DNA extraction is preferably accomplished by an anionic exchange column chromatographic method of extracting nucleic acid. In the alternative, a solvent extraction method, such as that disclosed in Example 1, may be employed.

EXAMPLE 1

In order to provide further guidance regarding the DNA extraction portion of the process of the present invention, an example will be provided.

Figure 7:
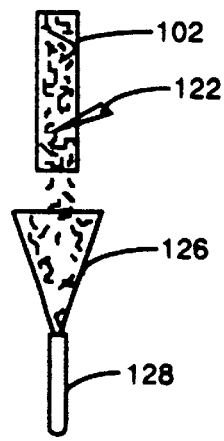
FIG. 7 is a schematic illustration of the use of DNA extraction in accordance with the present invention.

FIG. 7 illustrates DNA extraction for ParaFecogen. With reference to FIG. 7, a paraffin slide 102 with the paraffinophilic organisms growing on the surface is removed from tube 57 and first passed through three washings of sterile Czapek liquid broth. The paraffinophilic organisms growing on the surface of the paraffin slide are first scraped off the slide surface through funnel 126 into a sterile centrifuge tube 128 with a flame sterilized spatula 122. Five milliliters of sterile Czapek broth is then added to the tube. The centrifuge tube is then vortexed and placed in a refrigerated centrifuge chamber (4°C.) and spun for 15 min. at 10,000 rpm. The supernate is removed and discarded. The pellet is resuspended in 3 ml of Buffer #1 (10 mM Tris-HCl, 100 mM NaCl, 5 mM EDTA, pH 7.0) and vortexed. An aliquot of 15 mg lysozyme is added to a final concentration of 5.0 mg/ml. This is then incubated for 20 min. at 37° C. An aliquot of 2 ml of Buffer #2 (10 mM Tris-HCl, 250 mM NaCl, 1.2% Triton X-100, 100 µg/ml RNase A, 12 mM EDTA, 0.5 M Guanidine-HCl, pH 8.0) is added to the previous step and placed on ice for 20 min. An aliquot of 35 mg of Proteinase K is added to a final concentration of 7 mg/ml. This is then incubated at 50° C. for two hours. The centrifuge tube from the preceding step is then centrifuged at 15,000 rpm at 4° C. for 15 min. The supernate is carefully removed and transferred to a clean sterile centrifuge tube. The centrifuge tube is then again centrifuged at 15,000 rpm for 15 min. The supernate is carefully removed and transferred to a clean sterile centrifuge tube. The supernate is then again centrifuged at 15,000 rpm for 15 min. The supernate is then again carefully removed to a new sterile centrifuge tube. The supernate in this tube will now be referred to as the "lysate." To the lysate add an equal volume of Phenol-Chloroform (equal parts of re-distilled phenol mixed with chloroform-isoamyl alcohol (24:1) and equilibrate with 0.2 vol of 2M Tris, pH 7.0), followed by mixing vigorously by vortexing of tube. Centrifuge at 15,000 rpm for 20 min. at 20° C. Carefully transfer the upper aqueous phase to a new sterile centrifuge tube. Extract the aqueous phase once with 1 volume of chloroform-isoamyl alcohol (24:1, vol/vol) to remove residual phenol. Centrifuge at 15,000 rpm for 20 min. at 20° C. Transfer aqueous phase to new sterile centrifuge. Add ¹⁄₂₀ volume of 3 M Sodium Acetate to make the final concentration 0.3 M Sodium Acetate. Add two volumes of cold (−20° C.) 95% ethanol. Mix the solution well, and place at −20° C. overnight. Sediment the precipitated DNA by centrifugation at 15,000 rpm at 4° C. for 30 min. Remove the supernate and resuspend the pellet in 100 $\mu$l of sterile TE buffer (0.1M Tris-HCl (pH 8.0), 1.0 mM EDTA) or dd $H_2O$ (double distilled deionized water) and transfer to a sterile microcentrifuge tube. Store at −20° C. The resulting DNA can then be utilized with other DNA methodologies such as dot blot, southern blot, or gene amplification, such as is disclosed in U.S. Pat. Nos. 4,683,195; 4,683,202; 4,695,188 (the disclosures of which are incorporated herein by reference) to identify the presence of MAI sequences in the DNA pellet. Among the suitable genetic amplification systems employable in the present invention is that marketed under the trade designation Polymerase Chain Reaction (PCR) by Roche Corporation. This procedure provides the user with DNA that can be utilized with subsequent other applications, such as DNA amplification and the like.

An example of DNA extraction employing an alternate preferred means, column chromatography, will be considered.

EXAMPLE 2

Slides containing paraffinophilic organisms growing on the surface of the paraffin slide are first passed through three washings of sterile Czapek liquid broth. The paraffinophilic organisms growing on the surface of the paraffin slide are first scraped off the slide surface into a sterile centrifuge tube with a flame sterilized spatula. Five milliliters of sterile Czapek broth is then added to the tube. The centrifuge tube is then vortexed and placed in a refrigerated centrifuge chamber (4° C.) and spun for 15 min. at 10,000 rpm. The supernate is removed and discarded. The pellet is resuspended in 3 ml of Buffer #1 (10 mM Tris-HCl, 100 mM NaCl, 5 mM EDTA, pH 7.0) and vortexed. An aliquot of 15 mg lysozyme is added to a final concentration of 5.0 mg/ml. This is then incubated for 20 min. at 37° C. An aliquot of 2 ml of Buffer #2 (10 mM Tris-HCl, 250 mM NaCl, 1.2% Triton X-100, 100 $\mu$g/ml RNase A, 12 mM EDTA, 0.5M Guanidine-HCl, pH 8.0) is added to the previous step and placed on ice for 20 min. An aliquot of 35 mg of Proteinase K is added to a final concentration of 7 mg/ml. This is then incubated at 50° C. for two hours. The centrifuge tube from the preceding step is then centrifuged at 15,000 rpm at 4° C. for 15 min. The supernate is carefully removed and transferred to a clean sterile centrifuge tube. The centrifuge tube is then again centrifuged at 15,000 rpm for 15 min. The supernate is carefully removed and transferred to a clean sterile centrifuge tube. The supernate is then again centrifuged at 15,000 rpm for 15 min. The supernate is then again carefully removed to a new sterile centrifuge tube. The supernate in this tube will now be referred to as the "lysate." A 5 ml syringe barrel filled with a 1 ml slurry of DEAE-Sephadex A25 Anionic Chromatographic Gel Matrix (Pharmacia LKB Biotechnology, Inc., Piscataway, N.J. U.S.A.) or a Qiagen "Tip-20" chromatographic column available from Qiagen, Inc. (Qiagen, Inc., Chatsworth, Calif., U.S.A.) is equilibrated with 1 ml of Buffer #3 (750 mM NaCl, 50 mM MOPS, 15% Ethanol, 0.15% Triton-X-100, pH 7.0). The lysate is now applied to the Anionic Exchange Column Matrix (AECM). The AECM column is then washed with 4 ml of Buffer #4 (1000 mM NaCl, 50 mM MOPS, 15% Ethanol, pH 7.0). The AECM column is eluted with 1 ml of Buffer #5 (1250 mM NaCl, 50 mM Tris-HCl, 15% Ethanol, pH 8.5). After all the Buffer #5 has run through the AECM column, a 20 ml syringe is employed to remove the remaining buffer. The eluate obtained in this step is dispensed into aliquots of 500 $\mu$l in microcentrifuge tubes. Add 500 $\mu$l of isopropyl alcohol to each of the microcentrifuge tubes. Spin at 14,000 rpm for 30 min. at 4° C. Carefully remove supernate and discard. Add 1000 $\mu$l of 70% (v/v) ethanol per tube and spin at 14,000 rpm for 10 min. at 4° C. Carefully remove supernate and discard. Dry tubes at room temperature for 10 min. Resuspend the pellet in 100 $\mu$l of sterile TE buffer (0.1M Tris-HCl (pH 8.0), 1.0 mM EDTA) or dd $H_2O$ (double distilled deionized water) and transfer to a sterile microcentrifuge tube. Store at −20° C. This provides the user with DNA that can be utilized with subsequent other applications, such as DNA amplification and the like.

It will be appreciated that the foregoing system provides an improved means for rapidly and effectively isolating and identifying paraffinophilic MAI organisms present in a body specimen.

It will be appreciated that while a substantial portion of the disclosure has focused on the isolating and identifying of MAI, with particular emphasis on employing fecal matter as the body specimen, the invention is not so limited. In its broader aspects, the invention may be employed with other body specimens and may be employed to detect the presence of other types of paraffinophilic matter in the specimen.

Whereas particular embodiments of the invention have been described herein for purposes of illustration, it will be evident to those skilled in the art that numerous variations of the details may be made without departing from the invention as defined in the appended claims.

What is claimed is:

1. A method of determining the presence of a paraffinophilic microorganism in a body specimen, said method comprising:

introducing portions of said body specimen into a plurality of receptacles containing a sterile broth;

introducing a slide coated with a layer of paraffin into said receptacle;

observing said slide for the presence of a paraffinophilic microorganism growing thereon;

removing at least a portion of said layer of paraffin including said paraffinophilic microorganism growing on said slide;

extracting a purified DNA fraction from said removed layer of paraffin including said paraffinophilic microorganism growing on said slide; and determining from said purified DNA fraction whether a paraffinophilic microorganism is present in said body specimen.

2. The method of claim 1, including extracting said purified DNA fraction from said removed layer of paraffin including said paraffinophilic microorganism growing on said slide by the following steps:

adding a lysozyme to said removed layer of paraffin including said paraffinophilic microorganism to create a crude lysate;

separating cellular debris from said crude lysate to create a solution containing proteins and nucleic acid;

destroying said proteins in said solution to create a crude DNA fraction;

separating particulate matter from said crude DNA fraction to create a crude DNA solution; and introducing said crude DNA solution into an anionic column chromatograph in order to obtain a purified DNA solution.

3. The method of claim 2, including destroying said proteins by adding Proteinase K to said solution containing proteins and nucleic acid.

4. The method of claim 1, including employing said method on at least one body specimen selected from the group consisting of fecal matter, blood, sputum, tissue and cerebral spinal fluid.

5. The method of claim 4 including employing said method to test a fecal specimen of a human being to determine if said human being has MAI or other paraffinophilic organism.

6. The method of claim 1 including employing said method to test for at least one member of the group consisting of *Micrococcus paraffinae; Corynebacterium simplex;* Ahnl; *Mycococcus* (Rhodococcus) *cinnabareus;* Ahnl. *Mycococcus* (Rhodoc) *rhodochrous; Mycobact. perrugosum* Var. *athanicum; Mycobact. rubrum* Var. *propanicum; Mycobacterium hyalinum; Mycobacterium lacticola; Mycobacterium album. M. luteum; Mycobacterium microti; Mycobacterium rubrum, Mycobacterium phlei.; Mycobacterium phlei, M. smegmatis; Mycobacterium testudo; Mycobacterium-avium-intracellulare;*Nocardia Spp.; Actinomyces; *Candida lipolytica; Candida tropicalis, Torulopsis colliculosa;* Monilia Sp., Hansenula Sp., *Torula rossa;* Penicillium Sp.; IHNL. *Aspergillus flavus;* Aspergillus sp., Penicillium Sp.; Citromyces Sp., Scopulariopsis Sp.; *Pseudomonas fluorescens liquefaciens;* Ahnl, *Pem. fluorescens denitrificans;* and *Pseudomonas aeruginosa.*

7. The method of claim 6 including employing said method on a human body specimen.

8. The method of claim 7 including employing said method on a human fecal specimen to determine if said human has said paraffinophilic organism.

9. The method of claim 8 including employing said method to determine if said human has MAI.

10. The method of claim 1 including providing an antibiotic in said receptacle.

11. A method of obtaining a purified DNA fraction from a paraffinophilic microorganism growing on a slide coated with a layer of paraffin, said method comprising:

removing at least a portion of said layer of paraffin including said paraffinophilic microorganism growing on said slide;

adding a lysozyme to said removed layer of paraffin including said paraffinophilic microorganism to create a crude lysate;

separating cellular debris from said crude lysate to create a solution containing proteins and nucleic acid;

destroying said proteins in said solution to create a crude DNA fraction;

separating particulate matter from said crude DNA fraction to create a crude DNA solution; and introducing said crude DNA solution into an anionic column chromatograph in order to obtain a purified DNA fraction.

12. The method of claim 11 including destroying said proteins by adding Proteinase K to said solution containing proteins and nucleic acid.

* * * * *